(12) United States Patent
Borkholder et al.

(10) Patent No.: US 9,138,172 B2
(45) Date of Patent: Sep. 22, 2015

(54) METHOD FOR MONITORING EXPOSURE TO AN EVENT AND DEVICE THEREOF

(75) Inventors: David A. Borkholder, Canandaigua, NY (US); Brian Derek DeBusschere, Los Gatos, CA (US)

(73) Assignee: Rochester Institute of Technology, Rochester, NY (US)

( * ) Notice: Subject to any disclaimer, the term of this patent is extended or adjusted under 35 U.S.C. 154(b) by 802 days.

(21) Appl. No.: 13/371,226

(22) Filed: Feb. 10, 2012

(65) Prior Publication Data

US 2012/0239342 A1    Sep. 20, 2012

Related U.S. Application Data

(60) Provisional application No. 61/446,376, filed on Feb. 24, 2011.

(51) Int. Cl.
*A61B 5/11* (2006.01)
*A61B 5/00* (2006.01)

(52) U.S. Cl.
CPC ............... *A61B 5/11* (2013.01); *A61B 5/4064* (2013.01); *A61B 5/7275* (2013.01); *A61B 2560/0242* (2013.01)

(58) Field of Classification Search
CPC ........................................................ A61B 5/11
USPC ....................................................... 702/138
See application file for complete search history.

(56) References Cited

U.S. PATENT DOCUMENTS

| | | | |
|---|---|---|---|
| 5,884,203 A | 3/1999 | Ross | |
| 6,125,686 A | 10/2000 | Haan et al. | |
| 6,285,031 B1 | 9/2001 | Listl et al. | |
| 6,307,481 B1 | 10/2001 | Lehrman et al. | |
| 6,501,386 B2 | 12/2002 | Lehrman et al. | |
| 6,661,347 B2 | 12/2003 | Lehrman et al. | |
| 6,703,939 B2 | 3/2004 | Lehrman et al. | |
| 6,730,047 B2 | 5/2004 | Socci et al. | |
| 6,864,796 B2 | 3/2005 | Lehrman et al. | |
| 6,887,202 B2 | 5/2005 | Currie et al. | |
| 6,941,952 B1 | 9/2005 | Rush, III | |
| 7,095,331 B2 | 8/2006 | Lehrman et al. | |
| 7,145,461 B2 | 12/2006 | Lehrman et al. | |
| 7,335,168 B2 | 2/2008 | Rugg | |
| 7,384,380 B2 | 6/2008 | Reinbold et al. | |
| 7,479,890 B2 | 1/2009 | Lehrman et al. | |

(Continued)

FOREIGN PATENT DOCUMENTS

WO    2009026903 A1    3/2009

OTHER PUBLICATIONS

International Search Report for International Patent Application No. PCT/US2012/026625 (Sep. 21, 2012).

*Primary Examiner* — Bryan Bui
(74) *Attorney, Agent, or Firm* — Joseph M. Noto; Bond, Schoeneck & King PLLC

(57) ABSTRACT

A method, non-transitory computer readable medium, and apparatus that includes obtaining, by a dosimetry computing device, sensor readings from at least one sensor. An event is identified, by the dosimetry computing device, based on at least one of one or more of the obtained sensor readings or one or more determinations based on the obtained sensor readings meeting one or more selection. At least one of the one or more determinations or the sensor readings which meet one or more of the selection criteria when the event is identified is stored by the dosimetry computing device.

81 Claims, 2 Drawing Sheets

(56) References Cited

U.S. PATENT DOCUMENTS

| | | |
|---|---|---|
| 7,609,156 B2 | 10/2009 | Mullen |
| 7,627,451 B2 | 12/2009 | Vock et al. |
| 7,693,668 B2 | 4/2010 | Vock et al. |
| 7,747,415 B1 | 6/2010 | Churchill et al. |
| 7,836,771 B2 | 11/2010 | Killion |
| 7,992,421 B2 | 8/2011 | Jeftic-Stojanovski et al. |
| 8,056,391 B2 | 11/2011 | Petelenz et al. |
| 8,079,247 B2 | 12/2011 | Russell et al. |
| 8,145,441 B2 | 3/2012 | Xi |
| 2004/0200967 A1 | 10/2004 | Russell |
| 2005/0177335 A1 | 8/2005 | Crisco, III et al. |
| 2006/0074338 A1 | 4/2006 | Greenwald et al. |
| 2006/0189852 A1 | 8/2006 | Greenwald et al. |
| 2007/0079149 A1 | 4/2007 | Sahu et al. |
| 2008/0072008 A1 | 3/2008 | Garst et al. |
| 2008/0151456 A1 | 6/2008 | Julicher |
| 2008/0281234 A1 | 11/2008 | Goris et al. |
| 2010/0016685 A1 | 1/2010 | Muehlsteff et al. |
| 2010/0072380 A1 | 3/2010 | Britton, Jr. et al. |
| 2010/0096556 A1 | 4/2010 | Arsalan et al. |
| 2010/0102970 A1 | 4/2010 | Hertz |
| 2010/0121226 A1 | 5/2010 | Ten Kate et al. |
| 2010/0171514 A1 | 7/2010 | Bernstein |
| 2010/0179389 A1 | 7/2010 | Moroney, III et al. |
| 2010/0229784 A1 | 9/2010 | Bayne et al. |
| 2010/0275676 A1 | 11/2010 | King et al. |
| 2011/0012759 A1 | 1/2011 | Yin |
| 2011/0077865 A1 | 3/2011 | Chen et al. |
| 2011/0098934 A1 | 4/2011 | Hubler et al. |
| 2011/0144539 A1 | 6/2011 | Ouchi |
| 2011/0144542 A1 | 6/2011 | Jin et al. |
| 2011/0152727 A1 | 6/2011 | Ten Kate |
| 2011/0162433 A1 | 7/2011 | Peng et al. |
| 2011/0181418 A1 | 7/2011 | Mack et al. |
| 2011/0181419 A1 | 7/2011 | Mack et al. |
| 2011/0181420 A1 | 7/2011 | Mack et al. |
| 2011/0184319 A1 | 7/2011 | Mack et al. |
| 2011/0199216 A1 | 8/2011 | Flinsenberg et al. |
| 2011/0201972 A1 | 8/2011 | Ten Kate |
| 2011/0203347 A1 | 8/2011 | Hower et al. |
| 2011/0215931 A1 * | 9/2011 | Callsen et al. ............. 340/573.1 |
| 2011/0230791 A1 | 9/2011 | Ten Kate et al. |
| 2011/0231145 A1 | 9/2011 | Chen |
| 2011/0246114 A1 | 10/2011 | Jin |
| 2011/0283791 A1 | 11/2011 | Jeftic-Stojanovski et al. |
| 2011/0290018 A1 | 12/2011 | Jeftic-Stojanovski et al. |
| 2012/0109575 A1 | 5/2012 | Balbus et al. |
| 2013/0118255 A1 * | 5/2013 | Callsen et al. .................. 73/491 |

\* cited by examiner

METHOD FOR MONITORING EXPOSURE TO AN EVENT AND DEVICE THEREOF

This application claims the benefit of U.S. Provisional Patent Application Ser. No. 61/446,376 filed Feb. 24, 2011, which is hereby incorporated by reference in its entirety.

This invention was made with government support under contract no. HR0011-10-C-0095 awarded by the DARPA. The government has certain rights in the invention.

BACKGROUND

Traumatic brain injury (TBI) from an explosive blast remains a significant problem for military personnel, especially those involved in counter insurgency operations. Mild to moderate TBI may be difficult to detect immediately post event, with cognitive or motor deficits manifesting weeks or months post event.

Additionally, exposure to other types of blows and other types of events is a significant problem for other individuals as well. For example, recreational and professional athletes in many sport activities are routinely exposed to blows and other types of events with unknown individual or cumulative effects. Additionally, bike and motorcycle riders may experience some type of blow or other event by way of example only.

Currently, there is no widely deployed system to dose the exposure to an explosive blast, blow or other type of event. Given the nature of TBI, the wide variability in explosions, blows and other events and as well as the physical configurations during a blast events, and the variability in human response to each blast event, a widely deployed system to all personnel in a theater is needed to build a database of sufficient size to allow real-time dosimeter data to be used for triage and to monitor and assess military and non-military personnel depending on the particular application.

SUMMARY

A method for monitoring exposure to an event includes obtaining, by a dosimetry computing device, sensor readings from at least one sensor. An event is identified, by the dosimetry computing device based on at least one of one or more of the obtained sensor readings or one or more determinations based on the obtained sensor readings meeting one or more selection. At least one of the one or more determinations or the sensor readings which meet one or more of the selection criteria when the event is identified is stored by the dosimetry computing device.

A non-transitory computer readable medium having stored thereon instructions for monitoring exposure to an event comprising machine executable code which when executed by at least one processor, causes the processor to perform including obtaining sensor readings from at least one sensor. An event is identified based on at least one of one or more of the obtained sensor readings or one or more determinations based on the obtained sensor readings meeting one or more selection. At least one of the one or more determinations or the sensor readings which meet one or more of the selection criteria when the event is identified is stored.

A dosimetry apparatus includes a processor coupled to a memory, the processor configured to execute programmed instructions stored in the memory including obtaining sensor readings from at least one sensor. An event is identified based on at least one of one or more of the obtained sensor readings or one or more determinations based on the obtained sensor readings meeting one or more selection. At least one of the one or more determinations or the sensor readings which meet one or more of the selection criteria when the event is identified is stored.

This technology provides a number of advantages including providing a more effective and efficient event monitoring dosimetry apparatus. With this technology, event data from a blast or blow can be captured and utilized to guide triage and treatment of exposed individuals. Additionally, this technology can capture and provide event data that will help to provide a better understanding the mechanisms of traumatic brain injury resulting from an explosive blast or blow.

This technology can be used in a variety of different applications, such as for the military, sporting activities, and other daily activities by way of example only. For military applications, this technology could be helmet mounted, helmet strap mounted, worn on the torso, mounted within vehicle cabins, on vehicle exteriors and/or on building by way of example only. For sporting activities, this technology could be mounted within helmets, on helmet straps, on headbands, on caps, and/or on uniforms by way of example only. For daily activities, this could be mounted to helmets used for bicycles and motorcycles by way of example.

DETAILED DESCRIPTION

Figure 1:
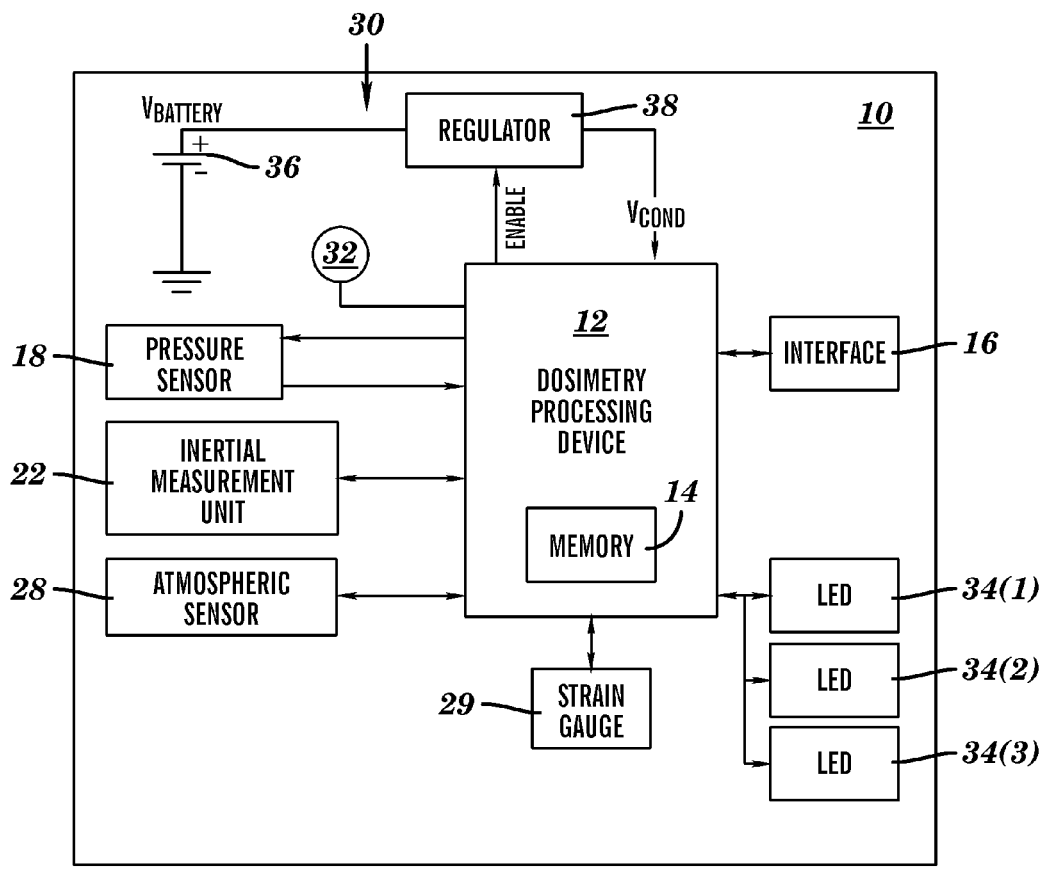
FIG. 1 is a diagram of an exemplary event monitoring dosimetry apparatus.

An exemplary event monitoring dosimetry apparatus 10 is illustrated in FIG. 1. This example of an event monitoring dosimetry apparatus 10 a dosimetry processing device 12 with a memory 14, an interface device 16, a pressure sensor 18, an inertial monitoring unit 22, an atmospheric sensor 28, a strain gauge 29, a power system 30, an engagement device 32, and a series of different colored LEDs with different numeric indicators 34(1)-34(3), although the apparatus 10 could include other types and numbers of systems, devices, components and elements in other configurations. This technology provides a number of advantages including provide a more effective and efficient event monitoring dosimetry apparatus.

Referring more specifically to FIG. 1, the dosimetry processing device 12 comprises one or more processors coupled to the memory 14 by a bus or other links, although other numbers and types of systems, devices, components, and elements in other configurations and locations can be used. The one or more processors in the dosimetry processing device 12 executes a program of stored instructions for one or more aspects of the present technology as described and illustrated by way of the examples herein, although other types and numbers of processing devices and logic could be used and the processor could execute other numbers and types of programmed instructions.

Figure 2:
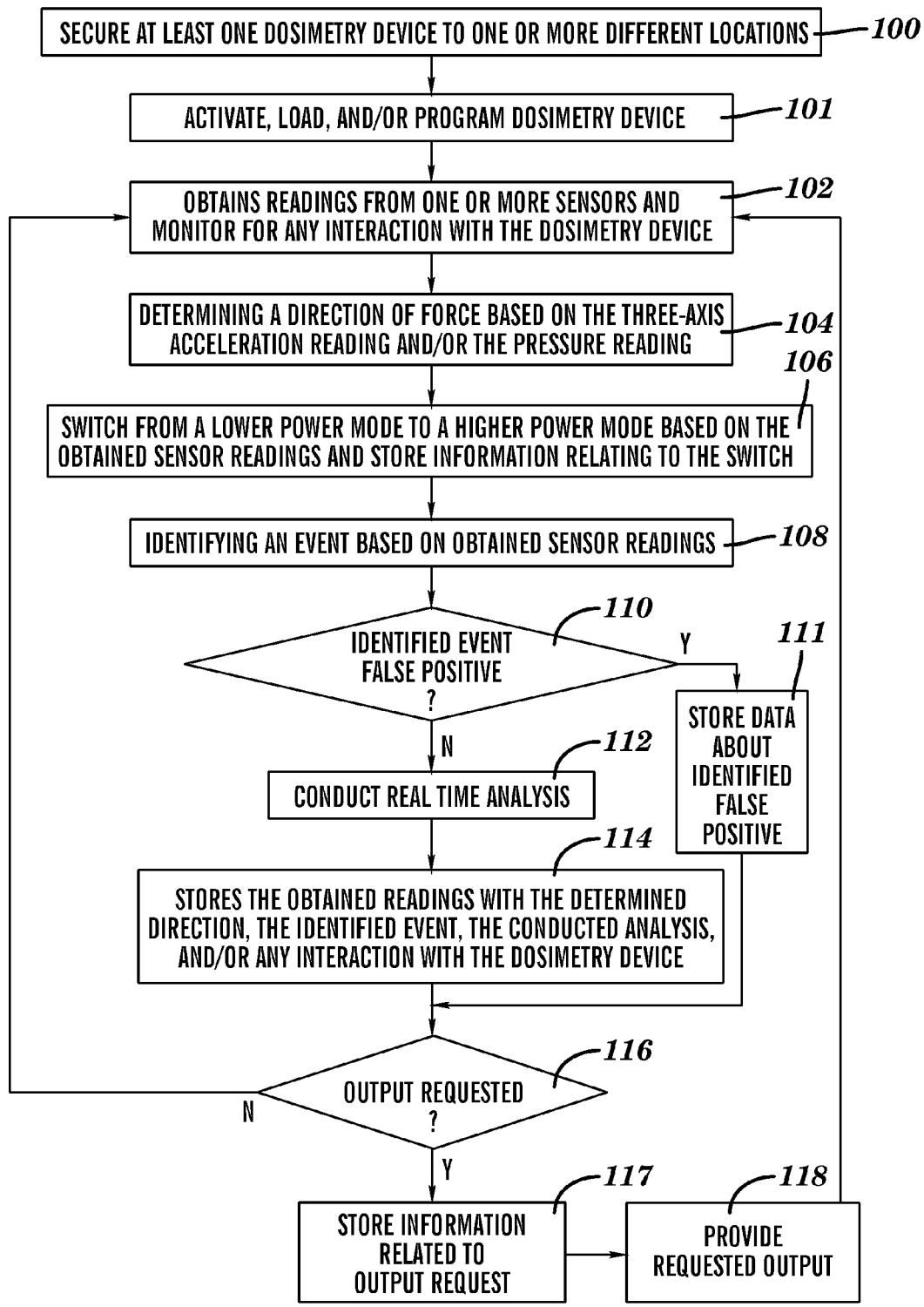
FIG. 2 is an exemplary method for monitoring events with the exemplary event monitoring dosimetry apparatus.

The memory 14 in the dosimetry processing device 12 stores these programmed instructions, data and other information for one or more aspects of the present technology as described and illustrated herein, although some or all of the programmed instructions could be stored and executed elsewhere. A variety of different types of memory storage devices, such as a solid state memory, can be used for the memory 14 in the dosimetry processing device 12. The flow chart shown in FIG. 2 is representative of example steps or actions of this technology that may be embodied or expressed as one or more non-transitory computer or machine readable instructions stored in memory 14 that may be executed by the one or more processors.

The interface device 16 in the dosimetry processing device 12 is used to operatively couple and communicate between the dosimetry processing device 12 and one or more external computing or storage devices, although other types and numbers of communication networks or systems with other types and numbers of connections and configurations can be used. In this example, the interface device 16 may be used to: (1) activate the dosimetry processing device 12 and load on time and date stamp; (2) adjust criteria and other parameters, (3) reprogram the dosimetry processing device 12, (4) extract data, such as stored readings, identified events, and/or any analysis, although the interface device can be utilized for other types and numbers of functions Although an example of the dosimetry processing device 12 is described herein, it can be implemented on any suitable computer system or computing device. It is to be understood that the devices and systems of the examples described herein are for exemplary purposes, as many variations of the specific hardware and software used to implement the examples are possible, as will be appreciated by those skilled in the relevant art(s).

Furthermore, the system of the examples may be conveniently implemented using one or more general purpose computer systems, microprocessors, digital signal processors, and micro-controllers, programmed according to the teachings of the examples, as described and illustrated herein, and as will be appreciated by those ordinary skill in the art.

The examples may also be embodied as a non-transitory computer readable medium having instructions stored thereon for one or more aspects of the present technology as described and illustrated by way of the examples herein, as described herein, which when executed by a processor, cause the processor to carry out the steps necessary to implement the methods of the examples, as described and illustrated herein.

The pressure sensor 18 is coupled to the dosimetry processing device 12, although the pressures sensor 18 could be coupled to other types and numbers of devices. In this example, the pressure sensor 18 is a single pressure sensor, although other types and numbers of pressure sensors could be used.

Referring back to FIG. 1, the inertial monitoring unit 22 is a low-g (for example 16 g) three-axis accelerometer to capture linear acceleration in three axes, although other types (for example a high-g 100 to 2000 g) and numbers of inertial measurement units could be used. For example, the inertial measurement unit 22 could be a gyroscope which records rotational acceleration. To account for differences in pressure readings from the pressure sensor 18 which depend on the incident direction of the force, the three-axis acceleration information from the inertial monitoring unit 22 can be used by the dosimetry processing device 12 to determine the vector of movement coincident with the arrival of the pressure shock front. This indicates the relative angle of the dosimetry apparatus 10 to the force allowing for compensation of the measured pressure profile including the levels of the stored reading thresholds to improve accuracy and precision with respect to the obtained readings and the identification of events. Additionally, if multiple dosimetry apparatuses 10 are used and are in communication with each other, the dosimetry processing device 12 could use time of flight differences to determine a direction of the blast or other event based on the pressure readings.

The atmospheric sensor 28 is coupled to the dosimetry processing device 12 and provides temperature, humidity, or light readings, although other types and numbers of environmental monitors could be used, the atmospheric sensor 28 could be positioned to take other readings, and the atmospheric sensor could be part of the dosimetry processing device 12. The dosimetry apparatus 10 also may include an optional strain gauge 29 coupled to provide stress measurement readings relating to a blast or other event to the dosimetry processing device 12, although other types and numbers of other sensors could be used.

The power system 30 includes a battery 36 coupled to a regulator 38 which is coupled to the dosimetry processing device 12, although other types of power systems with other types and numbers of components, such as one with an energy harvester and/or without a regulator 38 could be used. The regulator 38 is coupled to regulate power provided by the battery 36 to the dosimetry processing device 12. Additionally, in this example power for the pressure sensor 18, the inertial measurement unit 22, the atmospheric sensor 28, and/or the strain gauge 29 is coupled directly from the dosimetry processing device 12 to save power, although other types and numbers of devices and systems could be coupled directly to the dosimetry processing device 12 to provide power.

The engagement device 32, such as a button by way of example only, is coupled to the dosimetry processing device 12, although the engagement device could be coupled in other manners. The engagement device 32 can be used to request an output of readings including of identified events, stored events and/or assessments of the readings. Additionally, other types and numbers of mechanisms for engaging the dosimetry processing device 12 can be used, such as another computing device coupling to the dosimetry processing device 12 through the interface 16 to request and obtain output data and other information, download a time and date stamp, set and/or reprogram criteria and other parameters by way of example only.

The series of different colored LEDs with different numeric indicators 34(1)-34(3) are used to provide a status indication for the output stored readings and of the assessment of the stored readings associated with identified events to provide immediate triage of the severity of an event or to present an injury risk assessment, although other types and numbers of displays with other types of symbols which provide other types of outputs can be used. In this example, LED 34(1) is green colored and has a numeric indicator of zero, LED 34(2) is yellow colored and has a numeric indicator of one, and LED 34(1) is red colored and has a numeric indicator of two, although other colors and alphanumeric indicators or other symbols could be used.

Referring to FIG. 2, an exemplary method for monitoring events with the exemplary event monitoring dosimetry apparatus 10 will now be described. In step 100, at least one dosimetry apparatus 10 is secured to a location on an object, although other types and manners for securing the one or more dosimetry apparatuses 10 to the object can be used.

In step 101, the interface 16 of dosimetry processing device 12 can be used for a number of different types of functions, such as activating the dosimetry processing apparatus 10, loading a current time and date stamp into the dosimetry processing device 12, adding or modifying criteria and other parameter, and/or programming the dosimetry processing device 12 by way of example only. The engagement device 32 may also be used for activating the dosimetery processing apparatus 10. In this example, this step is illustrated at the start of this method, but this step can be performed at any time during this exemplary method.

In step 102, the dosimetry processing device 12 in the dosimetry apparatus 10 obtains readings from the at least one of the pressure sensor 18, the inertial measurement unit 22, atmospheric sensor 28, and/or the strain gauge 29, although the dosimetry apparatus 10 can obtain readings from other types and numbers of sensors. In this example, the pressure sensor 18 is a single pressure sensor which obtains pressure readings. Additionally, in this example, the inertial measurement unit 22 is a three-axis accelerometer which obtains linear acceleration readings in real time, although other types of inertial measurement units can be used, such as a gyroscope which obtains rotational acceleration readings. Further, the atmospheric sensor 28 can obtain one or more temperature, humidity, or ambient light readings in the dosimetry apparatus 10 which can be reviewed by the dosimetry processing device 12 and used to adjust one or more of the sensors, such as the pressure sensor 18, inertial measurement unit 22, atmospheric sensor 28, and/or strain gauge 29 by way of example only. The strain gauge 29 may obtain stress measurement readings resulting from a blast or other event and provide them to the dosimetry processing device 12. The dosimetry processing device 12 also may obtain and record one or more voltage measurements of the systems, devices and/or components in the dosimetry apparatus 10 which can be utilized to identify false positive events and for other diagnostics.

In step 104, the dosimetry processing device 12 optionally may for example determine a direction of the event based on the acceleration readings from three-axis accelerometer 22 and the pressure readings from the single pressure sensor 18 or in another example from pressure readings from multiple linked dosimetry apparatuses 10, although other manners for determining a direction of the event can be used. The dosimetry processing device 12 also may adjust threshold for injury risk assessment in memory 14 based on the determined direction of the event. For example to adjust the thresholds when body shielding has blocked some of the event or for impact directions where the body is more prone to injury.

In step 106, the dosimetry processing device 12 may switch from a lower power mode to a higher power mode based on identifying of one of the sensor readings which meet one or more of the selection criteria, although other manners for switching power modes can be used and there may be more than two different power modes. The dosimetry processing device 12 also may adjust the rate of obtaining the sensor readings in step 102 from a first sample rate in the lower power mode and a second sample rate which is higher than the first sample rate in the higher power mode, although other types of adjustments in sampling could be used.

In step 108, optionally the dosimetry processing device 12 may identify an event when at least one of the obtained pressure readings is above a stored pressure reading threshold in memory 14 and/or at least one of the acceleration readings is above a stored acceleration reading threshold in memory 14, although an event could be identified based on other readings and calculations and in other manners, for example by analyzing one or more pressure readings and one or more acceleration readings during an event time window. For example, the dosimetry processing device 12 might utilize an infinite impulse response (IIR) filter that allows both feed forward and feedback weighting coefficients to be implemented. An example of a high pass IIR filter that could be executed by the dosimetry processing device 12 is:

$$y(n) = \frac{1}{a_1}(-a_2 y(n-1) + b_1 x(n) + b_2 x(n-1))$$

where a and b coefficients are selected based on anticipated signal and noise waveform characteristics. In this approach, the filtered signal is used for triggering capture of an event based on y(n) exceeding a defined threshold value. An example of a low pass IIR persistence filter that could be executed by the dosimetry processing device 12 to identify an event is:

$$y(n) = y(n-1) + (1-\alpha)(x(n) - y(n-1))$$

where $\alpha$ is selected as described above. In this approach the filtered signal is used as a baseline against which real time measurements are compared. When the real time measurement exceeds the baseline y(n) by a defined threshold value, a capture event is identified. Alternate filtering techniques could also be leveraged for either approach.

The dosimetry processing device 12 also may identify an event when at least one of: one of the pressure readings is above the stored pressure threshold a set number of the pressure readings are above the stored pressure threshold; a first set number of pressure readings in a set is above a minimum stored threshold and below a maximum stored threshold for the set; a calculated pressure impulse from the pressure readings is above a stored pressure impulse threshold; at least one high pass filtered one of the pressure readings is above the stored pressure threshold as described above; at least one low pass filtered one of the pressure readings is above the stored pressure threshold; the pressure readings have a positive phase above a stored positive pressure threshold, followed by a negative phase below a stored positive pressure threshold by way of example only. Additionally, the dosimetry processing device 12 also may identify an event when at least one of: at least one of the acceleration readings has an acceleration value in an x, y, or z direction that is above a stored acceleration value threshold; a first set number of acceleration readings in the x, y, or z direction in a set is above a minimum stored threshold and below a maximum stored threshold for the set; at least one of the acceleration readings has an acceleration vector magnitude above a stored acceleration vector magnitude threshold; and at least one of the acceleration readings has a vector or axis acceleration impulse above a stored acceleration impulse threshold.

The dosimetry processing device 12 also may identify an event when at least one of: at least one of the acceleration readings has a rotational acceleration reading above a stored rotational acceleration threshold; at least one of the a first set number of rotational acceleration readings in a set is above a minimum stored threshold and below a maximum stored threshold for the set; rotational acceleration readings have an acceleration magnitude above a stored acceleration magnitude threshold; and/or at least one of the rotational acceleration readings has an acceleration impulse above a stored acceleration impulse threshold by way of example only.

Further, the dosimetry processing device 12 also may identify an event when one of the sensor readings is above a stored sensor threshold and a set number of subsequent sensor readings are which meet one or more of the selection criteria or when during an event time window one of the pressure readings is above a stored pressure criteria and one of the acceleration readings which corresponds with the one of the pressure readings is above a stored acceleration criteria.

In step 110, the dosimetry processing device 12 optionally may determine when the identified event is a false positive and then may store data related to the false positive event, such as peak recorded values although other types and amounts or data could be stored. By way of example only, the dosimetry processing device 12 may determined whether other related sensor readings within a set period of time also identify the event or may evaluate whether the obtained sensor readings that identified an event represent an anomaly signifying an false positive. If in step 110, the dosimetry processing device 12 determines the identified event is not a false positive, then the No branch is taken to step 112.

If in step 110, the dosimetry processing device 12 determines the identified event is a false positive, then the Yes branch is taken to step 111. In step 111, the dosimetry processing device 12 may store all of the data related to the false positive event in memory 14 or some other subset of the data and then proceeds to step 116.

In step 112, the dosimetry processing device 12 may conduct real time event analysis of the obtained pressure and/or acceleration readings and determine a injury risk assessment based on the conducted analysis, although other types and numbers of assessments based on other types and numbers of readings, such as from the atmospheric sensor 28 and/or the strain gauge 29 by way of example only, can be performed. In this example, the obtained readings may be compared by the dosimetry processing device 12 against stored tables of threshold readings in memory 14 to identify when one or more of the obtained readings are above the corresponding stored threshold reading in the table to identify an event. Additionally, the dosimetry processing device 12 assesses the severity of the event based on an amount the one or more of the obtained readings are above the corresponding stored threshold reading in the table, although other manners for conducting event analysis and determining a injury risk assessment can be used. The dosimetry processing device 12 stores the determined risk assessment in memory 14, although the determined risk assessments can be stored in other locations and manners.

In step 114, the dosimetry processing device 12 stores the obtained pressure readings from the pressure sensor 18, acceleration readings from the inertial measurement unit 22, atmospheric readings from the atmospheric sensor 28, stress measurement readings from the strain gauge 29, and/or the determined direction in memory 14, although other types and amounts of readings and other data could be stored, such as the identified one or more events, the determined injury risk assessment, and any interaction with or processing activity of the dosimetry processing device 12, such as through the engagement device 32 or the interface 16 as described earlier in step 101 by way of example, and in other locations and manners. Additionally, the dosimetry processing device 12 may store a record of any switch between a low power mode and a higher power mode with a time and date stamp when the switch occurred. The dosimetry processing device 12 may store any type of activity or change of state in the dosimetry apparatus 10, such as every time there was an acceleration reading above a stored threshold or all acceleration readings below a stored threshold for a certain period of time by way of example only. Further, the dosimetry processing device 12 may store a plurality of the identified events and other data as described herein up to a set limit, such as a capacity limit of memory 14, and then could replace one of the stored plurality of events with a next identified event when the set limit is reached based on one or more stored rules or storage retention criteria, such as identified events with lower severity assessments which may result in keeping the current stored plurality of events without adding the newly captured event and the dosimetry processing device 12 could retain all or a portion of the information, such as peak record values and/or a time and date stamp by way of example only, related to the rejected event in memory 14 or in other storage locations based on configuration of instructions on the dosimetry processing device 12.

In step 116, the dosimetry processing device 12 determines whether an output is requested, such as by activation of the engagement device 32 or a request via the interface 16, such as a USB, from another computing device, although other manners for output requests could be used. The activating of the engagement device could trigger a display on one of the LEDs 34(1)-34(3), although other types of outputs could be triggered, such as an output of data and other information. The engagement device 32 also can have other functions, such as providing outputting different information based on a number of times the button is pressed or the length of time the button is pressed or powering on or off the dosimetry apparatus 10. The request for data through the interface 16 from another computing device can be for all or requested portions of the stored data. If in step 116, the dosimetry processing device 12 determines an output has not been requested, then the No branch is taken back to step 102 as described earlier.

If in step 116, the dosimetry processing device 12 determines an output has been requested, then the Yes branch is taken to step 117. In step 117, the dosimetry processing device 12 may store information relating to the output request, such as a type of request, what data was requested, and a time and date of the request by way of example, although other types and amounts of data and information relating to the output request can be stored.

In step 118, the dosimetry processing device 12 provides the requested output, such as a display on one of the LEDs 34(1)-34(3) or an output of one or more of the stored readings, the identified event, a determined injury risk assessment based on the conducted analysis, data relating to switches between power modes, data relating to output requests, and/or identified false positive events and related data by way of example only via the interface 16, although the information could be output to other devices, other types and amounts of information and other data could be provided and the information and data can be obtained in other manners, such as through a connection with another computing device interacting with the dosimetry processing device 12 via the interface 16. In this example, the dosimetry processing device 12 can output the identified event with determined injury risk assessment based on the conducted analysis by illumination of one of the LEDs 34(1) with a numeric indicator in response to the activation by the engagement device 32, although other types and amounts of information could be provided. For example, if the determined injury risk assessment for the identified event is moderate, e.g. within a first range of one or more of the first thresholds then the yellow colored LED 34(2) with the numeric indicator of one is illuminated/flashed. If the determined injury risk assessment for the identified event is severe, e.g. above a first range of one or more of the first thresholds then the red colored LED 34(3) with the numeric indicator of two is illuminated/flashed. If there is no event recorded, the green colored LED 34(1) with the numeric indicator of zero is illuminated. Additionally, a requested output could trigger the dosimetry processing device 12 to output the stored readings, determined direction and other data described in the examples herein with or without the assessment information via the interface device 16 to another computing device. Next, this method can return back to step 102 until the exemplary dosimetry apparatus 10 is turned off or the power runs out.

Accordingly, as illustrated and described with reference to the examples herein this technology provides a more effective and efficient event monitoring dosimetry apparatus. With this technology, event data from a blast or blow can be captured and utilized to provide real time analysis for triage, and detailed analysis to guide treatment of exposed individuals. Additionally, this technology can capture and provide event data that will help to provide a better understanding the mechanisms of traumatic brain injury resulting from an explosive blast or blow. Further, this technology can be manufactured at a low cost to be disposable.

A data storage method stored as programmed instructions executed by the dosimetry processing device in this example captures high data rate pressure and acceleration data for a first period of time and low data rate acceleration data for a second period of time, although other time periods could be used. This approach allows response to the event to be captured, with resulting, slower bulk object movement captured while minimizing data storage requirements.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A method for monitoring exposure of an individual to an event, the method comprising:
   obtaining, by a dosimetry computing device comprising at least one pressure sensor, one or more sensor readings from the at least one sensor;
   identifying, by the dosimetry computing device, a blast event comprising a pressure shock front experienced by the individual based on at least one of the one or more obtained sensor readings or one or more determinations based on the one or more obtained sensor readings exceeding a defined trigger threshold value based on one or more selection criteria;
   determining a direction of the propagation of the blast event pressure shock front experienced by the at least one sensor; and
   storing, by the dosimetry computing device, at least one of the one or more determinations or the one or more obtained sensor readings which exceed one or more of the selection criteria when the blast event is identified.

2. The method of claim 1 wherein the storing further comprises storing, by the dosimetry computing device, all of the obtained sensor readings with a time and date stamp when the obtaining occurred.

3. The method of claim 1 wherein:
   the obtaining further comprises at least one of obtaining, by the dosimetry computing device, pressure readings from a pressure sensor or acceleration readings from an inertial measurement unit; and
   the identifying further comprising identifying, by the dosimetry computing device, the event when at least one of one of the pressure readings is above a stored pressure criteria or one of the acceleration readings is above a stored acceleration criteria.

4. The method of claim 3 wherein the identifying exceeding a trigger threshold comprises identifying, by the dosimetry computing device, the event based on at least one of: one of the pressure readings is above the stored pressure criteria; a set number of the pressure readings are above the stored pressure criteria; a first set number of pressure readings in a set is above a minimum stored criteria and below a maximum stored criteria for the set; a calculated pressure impulse from the pressure readings is above a stored pressure impulse criteria; at least one high pass filtered one of the pressure readings is above the stored pressure criteria; at least one low pass filtered one of the pressure readings is above the stored pressure criteria; the pressure readings have a positive phase above a stored pressure criteria, followed by a negative phase below a stored pressure criteria.

5. The method of claim 1 wherein the determining a direction of the blast event is based on at least one of: at least one of the acceleration readings has an acceleration value in an x, y, or z direction is above a stored acceleration value criteria; at least one of a first set number of acceleration readings in the x, y, or z direction in a set is above a minimum stored criteria and below a maximum stored criteria for the set; acceleration readings has an acceleration vector magnitude above a stored acceleration vector magnitude criteria; and at least one of the acceleration readings has a vector or axis acceleration impulse above a stored acceleration impulse criteria.

6. The method of claim 1 wherein the determining a direction of the blast event is based on at least one of: at least one of the acceleration readings has a rotational acceleration reading above a stored rotational acceleration criteria; at least one of a first set number of rotational acceleration readings in a set is above a minimum stored criteria and below a maximum stored criteria for the set; rotational acceleration readings have an acceleration magnitude above a stored acceleration magnitude criteria; and at least one of the rotational acceleration readings has an acceleration impulse above a stored acceleration impulse criteria.

7. The method of claim 1 wherein the determining a direction of the blast event comprises obtaining pressure readings above a stored pressure criteria from the at least one pressure sensor or from multiple linked dosimetry apparatuses and obtaining acceleration readings from a three-axis accelerometer above a stored acceleration criteria.

8. The method of claim 1 wherein the identifying further comprising identifying, by the dosimetry computing device, the event based on one of the sensor readings satisfies a stored sensor criteria and a set number of subsequent sensor readings satisfy at least one of the stored sensor criteria or additional stored sensor criteria.

9. The method of claim 1 further comprising identifying, by the dosimetry computing device, when the identified event is a false positive prior to the storing.

10. The method of claim 9 wherein the storing, further comprises storing, by the dosimetry computing device, at least one of the one or more determinations or the obtained readings related to the false positive identified event with a time and date stamp when the determining occurred.

11. The method of claim 1 further comprising switching, by the dosimetry computing device, from a lower power mode to a higher power mode based on the identifying of one of the sensor readings which meet one or more of the selection criteria.

12. The method of claim 11 further comprising:
   storing, by the dosimetry computing device, the switch with a time and date stamp when the switch occurred; and outputting, by the dosimetry computing device, in response to a request the stored switch with the time and date stamp when the switch occurred.

13. The method of claim 11 wherein the obtaining, by the dosimetry computing device, further comprises obtaining the sensor readings from at least one sensor at a first sample rate in the lower power mode and a second sample rate which is higher than the first sample rate in the higher power mode.

14. The method of claim 1 wherein the
determining a direction of the event comprises obtained acceleration readings from the at least one sensor comprising an acceleration sensor or obtained pressure readings from the at least one sensor comprising a plurality of pressure sensors each being separated by at least a first set distance.

15. The method of claim 14 further comprising:
assessing, by the dosimetry computing device, the event based on the identified sensor readings and the determined direction of the event; and
outputting, by the dosimetry computing device, the assessment of the event.

16. The method of claim 1 further comprising:
assessing, by the dosimetry computing device, the event based on the identified sensor readings; and
outputting, by the dosimetry computing device, the assessment of the event.

17. The method of claim 16 further comprising engaging, by the dosimetry computing device, one of a plurality of illumination indicators based on the assessment of the event.

18. The method of claim 17 wherein the engaging, by the dosimetry computing device, further comprises illuminating one of a plurality of symbols with the one of the plurality of illumination indicators based on the assessment of the event.

19. The method of claim 1 further comprising:
receiving, by the dosimetry computing device, at least one output request; and
outputting, by the dosimetry computing device, at least one of the one or more determinations or the obtained sensor readings which meet one or more of the selection criteria when the event is identified.

20. The method of claim 19 further comprising storing, by the dosimetry computing device, the received at least one output request with a time and date stamp when received, wherein the outputting further comprises outputting, by the dosimetry computing device, the stored output request with the time and date stamp when received.

21. The method of claim 1 further comprising:
receiving, by the dosimetry computing device, at least one output request; and
outputting, by the dosimetry computing device, at least one of the one or more determinations or the obtained sensor readings with the time and date stamp when each is obtained in response to the received at least one output request.

22. The method of claim 21 further comprising storing, by the dosimetry computing device, the received at least one output request with a time and date stamp when received, wherein the outputting further comprises outputting, by the dosimetry computing device, the stored output request with the time and date stamp when received.

23. The method of claim 1 further comprising:
recording, by the dosimetry computing device, at least one of one or more atmospheric measurements in the housing by at least one atmospheric sensor coupled to the dosimetry computing device or one or more voltage measurements of the dosimetry computing device.

24. The method of claim 1 further comprising:
storing, by the dosimetry computing device, at least a portion of obtained readings or calculations for each of a plurality of the identified events up to a set limit; and
replacing, by the dosimetry computing device, one of the stored plurality of events with a next identified event when the set limit is reached based on one or more stored retention criteria.

25. The method of claim 1 further comprising:
capturing, by the dosimetry computing device, one or more environmental parameters by an atmospheric sensor;
adjusting, by the dosimetry computing device, the stored sensor criteria based on the captured one or more environmental parameters.

26. A non-transitory computer readable medium having stored thereon instructions for monitoring exposure to an event comprising machine executable code which when executed by at least one processor, causes the processor to perform steps:
obtaining sensor readings from at least one sensor of a dosimetry device comprising at least one pressure sensor;
identifying a blast event comprising a pressure shock front experienced by an individual based on the obtained sensor readings or one or more determinations based on the obtained sensor readings exceeding a defined trigger threshold value based on one or more selection criteria;
determining a direction of the propagation of the blast event pressure shock front experienced by the at least one sensor; and
storing at least one of the one or more determinations or the obtained sensor readings which exceed one or more of the selection criteria when the blast event is identified.

27. The medium of claim 26 wherein the storing further comprises storing all of the obtained sensor readings with a time and date stamp when the obtaining occurred.

28. The medium of claim 26 wherein:
the obtaining further comprises at least one of obtaining pressure readings from a pressure sensor or acceleration readings from an inertial measurement unit; and
the identifying further comprises identifying the event when at least one of one of the pressure readings is above a stored pressure criteria or one of the acceleration readings is above a stored acceleration criteria.

29. The medium of claim 26 wherein the identifying exceeding a trigger threshold comprises identifying the event based on at least one of: one of the pressure readings is above the stored pressure criteria; a set number of the pressure readings are above the stored pressure criteria; a first set number of pressure readings in a set is above a minimum stored criteria and below a maximum stored criteria for the set; a calculated pressure impulse from the pressure readings is above a stored pressure impulse criteria; at least one high pass filtered one of the pressure readings is above the stored pressure criteria; at least one low pass filtered one of the pressure readings is above the stored pressure criteria; the pressure readings have a positive phase above a stored pressure criteria, followed by a negative phase below a stored pressure criteria.

30. The medium of claim 26 wherein the determining a direction of the blast event is based on at least one of: at least one of the acceleration readings has an acceleration value in an x, y, or z direction is above a stored acceleration value criteria; at least one of a first set number of acceleration readings in the x, y, or z direction in a set is above a minimum stored criteria and below a maximum stored criteria for the set; acceleration readings has an acceleration vector magnitude above a stored acceleration vector magnitude criteria; and at least one of the acceleration readings has a vector or axis acceleration impulse above a stored acceleration impulse criteria.

31. The medium of claim 26 wherein the determining a direction of the blast event is based on at least one of: at least one of the acceleration readings has a rotational acceleration reading above a stored rotational acceleration criteria; at least one of a first set number of rotational acceleration readings in a set is above a minimum stored criteria and below a maximum stored criteria for the set; rotational acceleration readings have an acceleration magnitude above a stored acceleration magnitude criteria; and at least one of the rotational acceleration readings has an acceleration impulse above a stored acceleration impulse criteria.

32. The medium of claim 26 wherein the determining a direction of the blast event comprises obtaining pressure readings above a stored pressure criteria from the at least one pressure sensor or from multiple linked dosimetry apparatuses and obtaining acceleration readings from a three-axis accelerometer above a stored acceleration criteria.

33. The medium of claim 26 wherein the identifying further comprising identifying the event based one of the sensor readings satisfies a stored sensor criteria and a set number of subsequent sensor readings satisfy at least one of the stored sensor criteria or additional stored sensor criteria.

34. The medium of claim 26 further comprising identifying when the identified event is a false positive prior to the storing.

35. The medium of claim 34 wherein the storing, further comprises storing at least one of the one or more determinations or the obtained readings related to the false positive identified event with a time and date stamp when the determining occurred.

36. The medium of claim 26 further comprising switching from a lower power mode to a higher power mode based on the identifying of one of the sensor readings which meet one or more of the selection criteria.

37. The medium of claim 36 further comprising:
storing the switch with a time and date stamp when the switch occurred; and
outputting in response to a request the stored switch with the time and date stamp when the switch occurred.

38. The medium of claim 36 wherein the obtaining further comprises obtaining the sensor readings from at least one sensor at a first sample rate in the lower power mode and a second sample rate which is higher than the first sample rate in the higher power mode.

39. The medium of claim 26 wherein the determining a direction of the event comprises obtained acceleration readings from the at least one sensor comprising an acceleration sensor or obtained pressure readings from the at least one sensor comprising a plurality of pressure sensors each being separated by at least a first set distance.

40. The medium of claim 39 further comprising:
assessing the event based on the identified sensor readings and the determined direction of the event; and
outputting the assessment of the event.

41. The medium of claim 26 further comprising:
assessing the event based on the identified sensor readings; and
outputting the assessment of the event.

42. The medium of claim 41 further comprising engaging one of a plurality of illumination indicators based on the assessment of the event.

43. The medium of claim 42 wherein the engaging further comprises illuminating one of a plurality of symbols with the one of the plurality of illumination indicators based on the assessment of the event.

44. The medium of claim 26 further comprising:
receiving at least one output request; and
outputting at least one of the one or more determinations or the obtained sensor readings which meet one or more of the selection criteria when the event is identified.

45. The medium of claim 44 further comprising storing the received at least one output request with a time and date stamp when received, wherein the outputting further comprises outputting the stored output request with the time and date stamp when received.

46. The medium of claim 26 further comprising:
receiving at least one output request; and
outputting at least one of the one or more determinations or the obtained sensor readings with the time and date stamp when each is obtained in response to the received at least one output request.

47. The medium of claim 46 further comprising storing the received at least one output request with a time and date stamp when received, wherein the outputting further comprises outputting the stored output request with the time and date stamp when received.

48. The medium of claim 26 further comprising:
recording at least one of one or more atmospheric measurements in the housing by at least one atmospheric sensor coupled to the dosimetry computing device or one or more voltage measurements of the dosimetry computing device.

49. The medium of claim 26 further comprising:
storing at least a portion of obtained readings or calculations for each of a plurality of the identified events up to a set limit; and
replacing one of the stored plurality of events with a next identified event when the set limit is reached based on one or more stored retention criteria.

50. The medium of claim 26 further comprising:
capturing one or more environmental parameters by an atmospheric sensor;
adjusting the stored sensor criteria based on the captured one or more environmental parameters.

51. The medium of claim 26 further comprising:
adjusting the obtained sensor readings based upon orientation of the at least one sensor to the blast direction to determine the force of the blast event experienced by the individual; and
applying the adjusted sensor readings to stored injury threshold values to determine an injury risk assessment.

52. The medium of claim 51 wherein the adjusting the obtained sensor readings comprises compensating the measured pressure readings based on the relative angle of the pressure sensor in the dosimetry apparatus to the force to improve accuracy and precision of the experienced force.

53. A dosimetry apparatus comprising:
one or more processors coupled to a memory, the one or more processors configured to execute programmed instructions stored in the memory comprising:
obtaining sensor readings from at least one sensor;
identifying a blast event comprising a pressure shock front based on the obtained sensor readings or one or more determinations based on the obtained sensor readings exceeding a defined trigger threshold value based on one or more selection criteria;

determining a direction of the propagation of the blast event pressure shock front experienced by the at least one sensor; and storing at least one of the one or more determinations or the sensor readings which exceed one or more of the selection criteria when the blast event is identified.

54. The apparatus of claim 53 wherein the one or more processors are further configured to execute programmed instructions stored in memory for the storing further comprises storing all of the obtained sensor readings with a time and date stamp when the obtaining occurred.

55. The apparatus of claim 53 wherein the one or more processors are further configured to execute programmed instructions stored in memory for:

the obtaining further comprises at least one of obtaining pressure readings from a pressure sensor or acceleration readings from an inertial measurement unit; and the identifying further comprising identifying the event when at least one of one of the pressure readings is above a stored pressure criteria or one of the acceleration readings is above a stored acceleration criteria.

56. The apparatus of claim 53 wherein the one or more processors are further configured to execute programmed instructions stored in memory for the identifying exceeding a trigger threshold comprises identifying the event based on at least one of: one of the pressure readings is above the stored pressure criteria; a set number of the pressure readings are above the stored pressure criteria; a first set number of pressure readings in a set is above a minimum stored criteria and below a maximum stored criteria for the set; a calculated pressure impulse from the pressure readings is above a stored pressure impulse criteria; at least one high pass filtered one of the pressure readings is above the stored pressure criteria; at least one low pass filtered one of the pressure readings is above the stored pressure criteria; the pressure readings have a positive phase above a stored pressure criteria, followed by a negative phase below a stored pressure criteria.

57. The apparatus of claim 53 wherein the one or more processors are further configured to execute programmed instructions stored in memory for the determining a direction of the blast event is based at least one of: at least one of the acceleration readings has an acceleration value in an x, y, or z direction is above a stored acceleration value criteria; at least one of a first set number of acceleration readings in the x, y, or z direction in a set is above a minimum stored criteria and below a maximum stored criteria for the set; acceleration readings has an acceleration vector magnitude above a stored acceleration vector magnitude criteria; and at least one of the acceleration readings has a vector or axis acceleration impulse above a stored acceleration impulse criteria.

58. The apparatus of claim 53 wherein the one or more processors are further configured to execute programmed instructions stored in memory for the determining a direction of the blast event is based on at least one of: at least one of the acceleration readings has a rotational acceleration reading above a stored rotational acceleration criteria; at least one of a first set number of rotational acceleration readings in a set is above a minimum stored criteria and below a maximum stored criteria for the set; rotational acceleration readings have an acceleration magnitude above a stored acceleration magnitude criteria; and at least one of the rotational acceleration readings has an acceleration impulse above a stored acceleration impulse criteria.

59. The apparatus of claim 53 wherein the one or more processors are further configured to execute programmed instructions stored in memory for the determining a direction of the blast event comprises obtaining pressure readings above a stored pressure criteria from the at least one pressure sensor or from multiple linked dosimetry apparatuses and obtaining acceleration readings from a three-axis accelerometer above a stored acceleration criteria.

60. The apparatus of claim 53 wherein the one or more processors are further configured to execute programmed instructions stored in memory for the identifying further comprises identifying the event based one of the sensor readings satisfies a stored sensor criteria and a set number of subsequent sensor readings satisfy at least one of the stored sensor criteria or additional stored sensor criteria.

61. The apparatus of claim 53 wherein the one or more processors are further configured to execute programmed instructions stored in memory further comprises identifying when the identified event is a false positive prior to the storing.

62. The apparatus of claim 61 wherein the one or more processors are further configured to execute programmed instructions stored in memory for the storing further comprises storing at least one of the one or more determinations or the obtained readings related to the false positive identified event with a time and date stamp when the determining occurred.

63. The apparatus of claim 53 wherein the one or more processors are further configured to execute programmed instructions stored in memory for the switching further comprising switching from a lower power mode to a higher power mode based on the identifying of one of the sensor readings which meet one or more of the selection criteria.

64. The apparatus of claim 63 wherein the one or more processors are further configured to execute programmed instructions stored in memory further comprising:

storing the switch with a time and date stamp when the switch occurred; and outputting in response to a request the stored switch with the time and date stamp when the switch occurred.

65. The apparatus of claim 63 wherein the one or more processors are further configured to execute programmed instructions stored in memory for the obtaining further comprises obtaining the sensor readings from at least one sensor at a first sample rate in the lower power mode and a second sample rate which is higher than the first sample rate in the higher power mode.

66. The apparatus of claim 53 wherein the one or more processors are further configured to execute programmed instructions stored in memory wherein the determining a direction of the event comprises obtained acceleration readings from the at least one sensor comprising an acceleration sensor or obtained pressure readings from the at least one sensor comprising a plurality of pressure sensors each being separated by at least a first set distance.

67. The apparatus of claim 66 wherein the one or more processors are further configured to execute programmed instructions stored in memory further comprising:

assessing the event based on the identified sensor readings and the determined direction of the event; and outputting the assessment of the event.

68. The apparatus of claim 53 wherein the one or more processors are further configured to execute programmed instructions stored in memory further comprising:

assessing the event based on the identified sensor readings; and outputting the assessment of the event.

69. The apparatus of claim 67 wherein the one or more processors are further configured to execute programmed instructions stored in memory further comprising engaging one of a plurality of illumination indicators based on the assessment of the event.

70. The apparatus of claim 69 wherein the one or more processors are further configured to execute programmed instructions stored in memory for the engaging further comprises illuminating one of a plurality of symbols with the one of the plurality of illumination indicators based on the assessment of the event.

71. The apparatus of claim 53 wherein the one or more processors are further configured to execute programmed instructions stored in memory further comprising:
  receiving at least one output request; and
  outputting at least one of the one or more determinations or the obtained sensor readings which meet one or more of the selection criteria when the event is identified.

72. The apparatus of claim 71 wherein the one or more processors are further configured to execute programmed instructions stored in memory further comprising storing the received at least one output request with a time and date stamp when received, wherein the outputting further comprises outputting the stored output request with the time and date stamp when received.

73. The apparatus of claim 53 wherein the one or more processors are further configured to execute programmed instructions stored in memory further comprising:
  receiving at least one output request; and
  outputting at least one of the one or more determinations or the obtained sensor readings with the time and date stamp when each is obtained in response to the received at least one output request.

74. The apparatus of claim 73 wherein the one or more processors are further configured to execute programmed instructions stored in memory further comprising storing the received at least one output request with a time and date stamp when received, wherein the outputting further comprises outputting the stored output request with the time and date stamp when received.

75. The apparatus of claim 53 wherein the one or more processors are further configured to execute programmed instructions stored in memory further comprising:
  recording at least one of one or more atmospheric measurements in the housing by at least one atmospheric sensor coupled to the dosimetry computing device or one or more voltage measurements of the dosimetry computing device.

76. The apparatus of claim 53 wherein the one or more processors are further configured to execute programmed instructions stored in memory further comprising:
  storing at least a portion of obtained readings or calculations for each of a plurality of the identified events up to a set limit; and
  replacing one of the stored plurality of events with a next identified event when the set limit is reached based on one or more stored retention criteria.

77. The apparatus of claim 53 wherein the one or more processors are further configured to execute programmed instructions stored in memory further comprising:
  capturing one or more environmental parameters by an atmospheric sensor;
  adjusting the stored sensor criteria based on the captured one or more environmental parameters.

78. The method of claim 1 further comprising:
  adjusting the obtained sensor readings based upon orientation of the at least one sensor to the blast direction to determine the force of the blast event experienced by the individual; and
  applying the adjusted sensor readings to stored injury threshold values to determine an injury risk assessment.

79. The method of claim 78 wherein the adjusting the obtained sensor readings comprises compensating the measured pressure readings based on the relative angle of the pressure sensor in the dosimetry apparatus to the force to improve accuracy and precision of the experienced force.

80. The apparatus of claim 53 further comprising:
  adjusting the obtained sensor readings based upon orientation of the at least one sensor to the blast direction to determine the force of the blast event experienced by the individual; and
  applying the adjusted sensor readings to stored injury threshold values to determine an injury risk assessment.

81. The apparatus of claim 80 wherein the adjusting the obtained sensor readings comprises compensating the measured pressure readings based on the relative angle of the pressure sensor in the dosimetry apparatus to the force to improve accuracy and precision of the experienced force.

* * * * *